United States Patent
Sommer

(10) Patent No.: US 7,820,989 B2
(45) Date of Patent: Oct. 26, 2010

(54) METHOD AND APPARATUS FOR PERFORMING RADIATION TREATMENT

(75) Inventor: Andres Sommer, Langensendelbach (DE)

(73) Assignee: Siemens Aktiengesellschaft, Munich (DE)

( * ) Notice: Subject to any disclaimer, the term of this patent is extended or adjusted under 35 U.S.C. 154(b) by 817 days.

(21) Appl. No.: 11/200,596

(22) Filed: Aug. 9, 2005

(65) Prior Publication Data

US 2006/0058637 A1  Mar. 16, 2006

(30) Foreign Application Priority Data

Aug. 12, 2004 (DE) ........................ 10 2004 039 191

(51) Int. Cl.
*A61N 5/00* (2006.01)
*A61B 5/05* (2006.01)

(52) U.S. Cl. .................. 250/493.1; 250/494.1; 378/4; 378/65; 382/132; 600/411

(58) Field of Classification Search ............ 250/493.1, 250/505.1; 128/897; 378/4, 65
See application file for complete search history.

(56) References Cited

U.S. PATENT DOCUMENTS

| | | | |
|---|---|---|---|
| 6,104,779 A * | 8/2000 | Shepherd et al. ............. 378/65 |
| 6,125,164 A | 9/2000 | Murphy et al. |
| 6,279,579 B1 | 8/2001 | Riaziat et al. |
| 6,516,046 B1 | 2/2003 | Fröhlich et al. |
| 6,635,882 B1 | 10/2003 | Pavlovic et al. |
| 6,708,054 B2 * | 3/2004 | Shukla et al. ............... 600/411 |
| 2002/0085668 A1 | 7/2002 | Blumhofer et al. |
| 2002/0188194 A1 | 12/2002 | Cosman |
| 2003/0133602 A1 | 7/2003 | Bani-Hashemi |
| 2003/0225325 A1 | 12/2003 | Kagermeier et al. |
| 2004/0002641 A1 | 1/2004 | Sjogren et al. |
| 2005/0152495 A1 * | 7/2005 | Hesse ........................ 378/65 |
| 2006/0182326 A1 * | 8/2006 | Schildkraut et al. ......... 382/132 |
| 2007/0153969 A1 * | 7/2007 | Maschke ...................... 378/4 |

FOREIGN PATENT DOCUMENTS

DE  198 05 917 A1  11/1999
DE  199 04 675 A1  8/2000

(Continued)

OTHER PUBLICATIONS

European Patent Office Action dated Dec. 1, 2005 and English translation.

(Continued)

*Primary Examiner*—David A Vanore
(74) *Attorney, Agent, or Firm*—Brinks, Hofer, Gilson & Lione

(57) ABSTRACT

A method is provided for determining and monitoring parameters of a radiation treatment. The method comprises producing a first image of a region of a patient body to be radiated using a medical imaging process, determining a parameter setting of a radiation system using the first image, and providing the radiation treatment to the body region to be radiated using the radiation system with the determined parameter setting. The method further comprises producing a second image of the body region radiated with the parameter setting, automatically comparing the first image and the second image, and generating a deviation signal when a difference between the first image and the second image exceeds a predetermined threshold value.

10 Claims, 1 Drawing Sheet

FOREIGN PATENT DOCUMENTS

Figure 1:
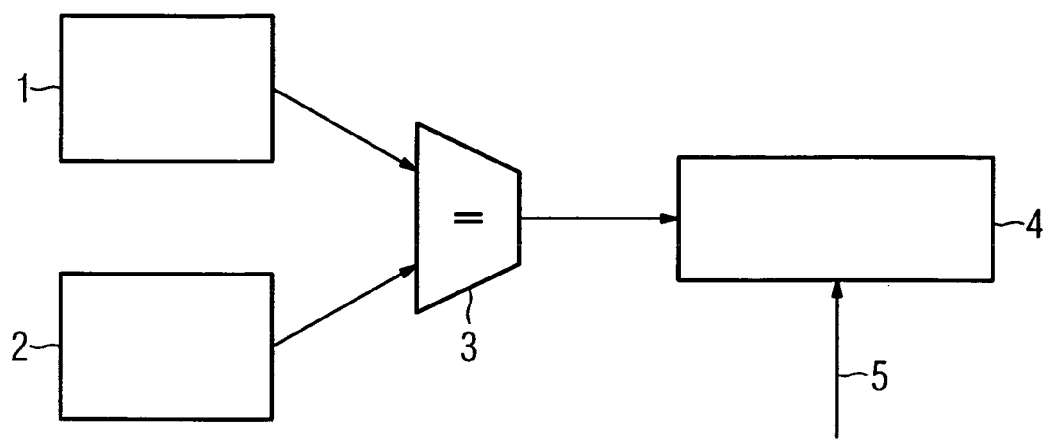

| | | |
|---|---|---|
| DE | 201 09 313 | 8/2001 |
| DE | 100 33 063 A1 | 1/2002 |
| DE | 103 01 075 A1 | 8/2003 |
| DE | 102 10 050 A1 | 12/2003 |
| EP | 0 465 590 B1 | 2/1996 |
| EP | 1 380 262 | 1/2004 |
| WO | WO 01/60236 | 8/2001 |
| WO | WO 03/076003 | 9/2003 |

OTHER PUBLICATIONS

European International Search Report dated Dec. 1, 2005 and English translation.
German Office Action dated Apr. 29, 2005 for DE 10 2004 039 191.2 and English translation.

* cited by examiner

METHOD AND APPARATUS FOR PERFORMING RADIATION TREATMENT

BACKGROUND

The embodiments relate, in general, to radiation systems, and more particularly, to a method and an apparatus for determining and monitoring parameters of a radiation treatment or therapy system.

A radiation system is known, for instance from German Patent Disclosure DE 199 04 675 A1. Before a radiation therapy is performed, regions of a patient body to be radiated are typically examined using a medical imaging method, such as computed tomography or CT. Images made of the patient, immobilized in the body region to be examined, are stored in memory as a data set. With the aid of this data set, parameter settings of a radiation system are made, such as the ones pertaining or corresponding to fields or radiation types. Simulating a radiation treatment, before the radiation system is programmed may also be possible. In performing the radiation treatment, a geometry and other properties of a tissue or body region to be radiated have assumingly not changed since examination and diagnosis via the imaging method. If properties of the tissue to be radiated do change in the course of the radiation therapy, a consequence is that the selected parameter setting of the radiation system may now be less adapted to the requirements of the radiation treatment.

From German Patent Disclosure DE 102 10 050 A1, a method for repositioning a patient in a diagnostic/therapeutic system, as well as such a system, are known. In an initial session, reference images are made of the patient, or part of the patient, using two video cameras. In a subsequent session, these reference images are compared with current images, and the position of the patient is changed until visible differences in position have been minimized.

OBJECT AND SUMMARY

The present invention is defined by the appended claims. This description summarizes some aspects of the present embodiments and should not be used to limit the claims.

A relatively simple, and reliable monitoring of a radiation therapy or treatment may be provided. All the features and advantages recited below in conjunction with the method apply accordingly to an apparatus, and vice versa.

Before the radiation therapy or treatment is performed, a first image is made of the tissue to be radiated, using an imaging method, such as a CT method. With the aid of this first image, a first parameter setting is made of a radiation system, such as a LINAC, or a particle radiation scanner. This first parameter setting can be done manually, partly automatically, or fully automatically, using image data. With the first parameter setting thus defined, the tissue now to be treated is radiated. After one or more radiation treatments, at least a second image is made of the tissue to be radiated, using the imaging method. These images made at various times are automatically compared, and a decision maker automatically generates a deviation signal, in the event of a deviation in the images that exceeds at least one threshold value. This deviation signal instructs a user of the radiation system that the properties of the tissue to be radiated have changed in such a way that the parameter setting may also be changed. The at least one threshold value, which determines when the deviation signal is generated, may be adjustable. As such, the user may adjust a sensitivity of the monitoring of changes in the tissue to be radiated, linked with monitoring of the parameter setting of the radiation system, and depending on the body region affected.

The comparison of the images on which the parameter setting is based may pertain to both a target area of the radiation treatment, typically a tumor, and to the tissue located in an irradiation direction outside the target area. From both the target area and from the tissue to be radiated located outside the target area, geometric properties and other properties, such as attenuation or density values, are evaluated automatically. Relevant geometric properties are the location and shape of the tumor as well as its volume, and the distance in the irradiation direction through which radiation passes between the skin of the patient and the target area. As such, a plurality of threshold values can be adjusted independently, for instance pertaining to geometric values on one hand and to density values on another hand.

In one embodiment, the deviation signal generated via a comparator and decision maker may not only indicate that the parameter setting of the radiation system is to be changed but simultaneously generate a planning instruction for the parameter setting. This planning instruction may contribute substantially to simplifying use of the radiation system, while at the same time minimizing a risk of incorrect settings of parameters of the radiation system. A new parameter setting, recommended via fixedly predetermined or adjustable algorithms, can be subjected to automatic plausibility control.

In another embodiment, the parameter setting of the radiation system, upon a deviation beyond the threshold value between images taken of the tissue to be radiated at different times, is automatically adapted to the altered conditions. Moreover, the new parameter setting becomes operative only after being enabled by the user, which may provide additional control of the parameter change that is proposed automatically.

In another embodiment, images taken in the course of a radiation treatment, such as CT images, are not only used for determining changes in the radiated tissue, but may also be used, in a rational and at least partly automated way, for changing operating parameters of the radiation system in adaptation to the altered tissue structure.

Illustrative and exemplary embodiments of the invention are described in further detail below in reference to and in conjunction with the figures.

BRIEF DESCRIPTIONS OF THE DRAWINGS

Figure 2:
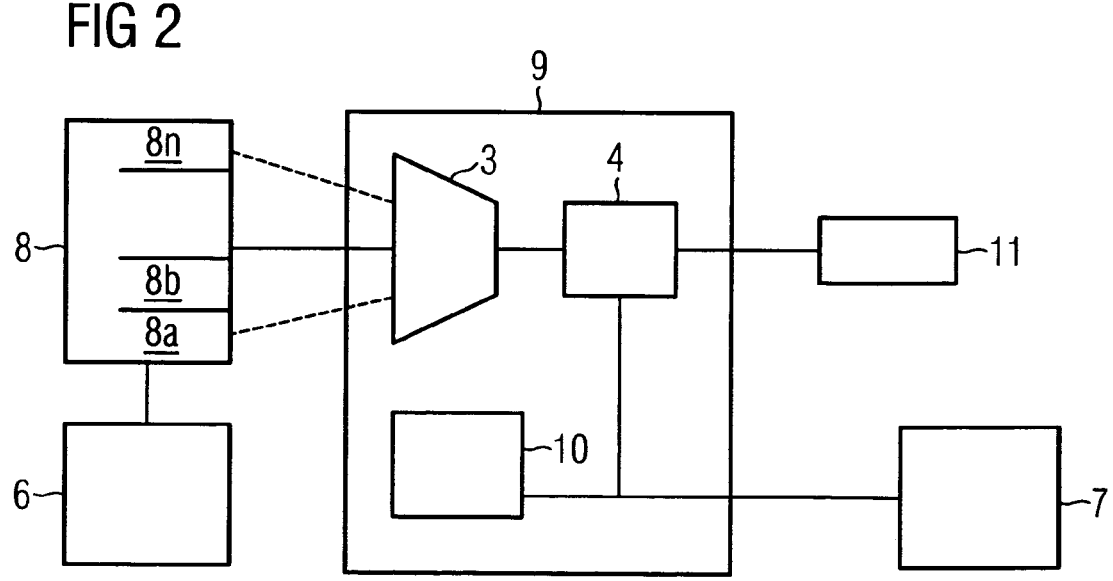

FIG. 1 is a flow diagram illustrating a method for monitoring parameters of a radiation treatment; and FIG. 2 is a block diagram illustrating one embodiment of an apparatus for performing a radiation therapy.

DETAILED DESCRIPTION OF THE DRAWINGS

Elements that correspond to one another are identified by the same reference numerals in both drawing figures.

In the diagram of FIG. 1, as a basis for planning a radiation therapy, multiple images of the target area to be irradiated are acquired or already exist. These images are made via a medical imaging method, such as CT or magnetic resonance methods, and are represented here as planning images 1 and current images 2. The images made in each examination, in the case of a CT examination, are also called a CT data set. Planning images 1 are made before the beginning of the radiation treatment and are used for setting parameters or a parameter set of the radiation system, such as a photon or particle radiation scanner. In setting the parameters of the radiation system, geometric properties and other properties that may influence radiation beams are taken into account, both for the target tissue or body region to be radiated, that is, the tumor, and the tissue that is likewise exposed to the radiation in the irradiation direction.

To determine whether the parameters of the radiation system are still suitably set, an automatic comparison may be made of the planning images 1 with the current images 2 that were made before and/or after one or more radiation treatments. The patient may have one radiation treatment a day, for instance. In the same way, CT images, made daily or at longer time intervals, of the tissue to be treated are made. In the case of proton beam therapy, the position is corrected with the aid of CT before every radiation treatment. The data obtained in the process can simultaneously be used for controlling the deviation of other parameters of the radiation treatment.

A comparator 3, which can access both the stored planning images 1 and the current images 2, is configured to perform the monitoring of the parameter setting of the radiation system, such as an ion radiation machine or a system that emits electromagnetic radiation. In the comparison, geometric characteristics, that is, the location and shape of the tumor as well as the surrounding tissue, and other characteristics, such as the tissue radiation absorption, are included. Depending on the degree of deviation between the at least one current image 2 and the at least one planning image 1, a decision maker 4 may determine whether the parameter setting of the radiation system is still suitable or should be changed. The threshold beyond which a change in the parameter setting is recommended is adjustable via at least one threshold value 5. If the threshold value is exceeded, a deviation signal, for instance a signal that can be processed by a data processing system and that may be formed of a plurality of individual signals of arbitrary formatting, is generated automatically. Signals optionally generated from the deviation signal, such as signals visually perceptible to the user, which indicate a change to be made in the parameter setting of the radiation system because of changes in the irradiated tissue, may be included.

When vulnerable tissues in the immediate vicinity of the tumor to be irradiated are present, the threshold value or values 5 may for instance be set substantially low. If the automatic comparison of the current images 2 with the planning images 1 shows that the threshold value or values have been exceeded, then the detected changes are shown, for instance by colored marking, on one of the images 1, 2, and in particular on t current images 2. Such pictorial visualization or display of the change in the irradiated tissue enables adjustments to the parameters or alternate settings of the parameters of the radiation system. These parameters may define the irradiation geometry and dose distribution in the tumor and surrounding tissues as well as the distribution over time of the total dose required for the radiation treatment. Accordingly, adapted parameter settings may be proposed to the user automatically by the radiation system described. The activity of the user in resetting the parameters of the radiation system, for instance setting fields and types of irradiation, can be limited to controlling and enabling the altered or adapted parameters.

The apparatus shown schematically in FIG. 2 for performing a radiation therapy has a coupling, in order to enable the above-described method, between an imaging diagnostic device 6, namely a CT scanner, and a radiation system 7 for tumor treatment. Images taken via or provided by the diagnostic device 6 are stored in an image memory 8, which has various memory regions 8a, 8b, . . . , 8n. For instance, planning images 1 are stored in memory region 8a, and current images 2 are stored in memory region 8n. As indicated by dashed lines, images 1 and 2 taken at various times are forwarded to comparator 3. Comparator 3 may be integral to a planning computer 9, which is shown as a closed unit in the schematic illustration but may equally comprise a plurality of linked together or coupled individual items of equipment. Without deviating from FIG. 2, image memory 8 may be part of planning computer 9, or may be combined from various components, as described below, of planning computer 9 to make unitary components. Moreover, both comparator 3 and the decision maker or controller 4 may be provided as software components of the radiation therapy system. In each case, planning computer 9 may serve, before the beginning of the radiation treatment, to determine a first parameter setting of radiation system 7 based on the first images, that is, the planning images 1.

The decision maker 4 connected to the comparator 3 has a connection with a parameter memory 10, in which the parameters for operating a radiation system that serves to treat tumors are stored. In parameter memory 10, various parameter settings can be stored, each adapted to characteristics of the tissue to be irradiated of which images were made at certain times. An association of the images 1 and 2, taken at various times and stored in the memory regions 8a . . . 8n, of the affected tissue regions of the patient, with the various parameter settings of the radiation system 7 that are stored in the parameter memory 10, thus documents data of the course of the radiation therapy in a readily comprehensible way. The therapy is also known as image-guided radiation therapy or adaptive radiation therapy (ART).

A sensitivity of the decision maker 4 can be reset as needed after each new image 1, 2. The corresponding threshold values 5 are input via an input device 11, which is part of planning computer 9 or is coupled to planning computer 9. Planning computer 9, as a function of characteristics of the tissue exposed to the radiation, may propose the threshold values 5 to the user or automatically set them. In each case, the automatic comparison of current images 2 with planning images 1 may assure a substantially high quality of the radiation treatment over an entire duration of the radiation therapy.

The invention claimed is:

1. A method for determining or monitoring parameters of a radiation treatment, the method comprising:
   producing, using a medical imaging process, a first image of a patient body region to be radiated;
   determining a parameter setting of a radiation system using the first image;
   treating with radiation the body region to be radiated using the radiation system with the determined parameter setting;
   producing a second image of the body region, the second image being produced after the radiation treatment;
   automatically comparing the first image and the second image, a shape of tissue in the first image being compared to a shape of tissue in the second image to determine a difference between the shape of the tissue to be radiated and the shape of the tissue that was radiated;
   generating a deviation signal when the difference exceeds a threshold value.

2. The method according to claim 1, wherein the threshold value is adjustable.

3. The method according to claim 1, wherein the second image is stored.

4. The method according to claim 1, wherein the automatic comparison of the first and second images corresponds to properties of a body region located in a direction of the radiation treatment and outside the body region.

5. The method according to claim 1, wherein the automatic comparison of the first and second images corresponds to beam-influencing properties of the body region.

6. The method according to claim 1, further comprising: generating planning instructions for the parameter setting of the radiation system as a function of the deviation signal.

7. The method according to claim 1, further comprising: automatically changing the parameter setting of the radiation system as a function of the deviation signal.

8. The method according to claim 1, wherein the automatic comparison of the first and second images corresponds to properties of a body region located in a direction of the radiation treatment and outside the body region.

9. The method according to claim 8 further comprising: generating planning instructions for the parameter setting of the radiation system as a function of the deviation signal.

10. A method for determining or monitoring parameters of a radiation treatment, the method comprising:
- producing, using a medical imaging process, a first image of a patient body region to be radiated;
- determining a parameter setting of a radiation system using the first image;
- treating with radiation the body region to be radiated using the radiation system with the determined parameter setting;
- producing a second image of the body region;
- automatically comparing a volume of tissue to be radiated in the first image and a volume of radiated tissue in the second image;
- generating a deviation signal when a difference between the first image and the second image exceeds a threshold value.

* * * * *